US00PP12493P2

(12) United States Plant Patent
Noodelijk

(10) Patent No.: US PP12,493 P2
(45) Date of Patent: Mar. 26, 2002

(54) CHRYSANTHEMUM NAMED 'RELINDA YELLOW'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/592,274

(22) Filed: Jun. 12, 2000

(51) Int. Cl.[7] ..... A01H 5/00
(52) U.S. Cl. ..... Plt./295
(58) Field of Search ..... Plt./295

*Primary Examiner*—Bruce R. Campell
*Assistant Examiner*—Annette H. Para
(74) *Attorney, Agent, or Firm*—Parkhurst & Wendel, LLP

(57) ABSTRACT

A Chrysanthemum plant named 'RELINDA YELLOW' characterized by its medium sized blooms with yellow ray-florets and a yellow-green cushion.

2 Drawing Sheets

RELATED CULTIVARS

'RELINDA YELLOW' is related to 'RELINDA' (U.S. plant patent application Ser. No. 09/592,273). 'RELINDA YELLOW' is a color mutant of 'RELINDA'.

BACKGROUND OF THE INVENTION

'RELINDA YELLOW' is a product of a breeding and selection program which had the objective of finding color mutants of RELINDA. The new plant of the present invention comprises a new and distinct cultivar of chrysanthemum plant that is a natural occuring sport of a parent chrysanthemum named RELINDA. A comparison with Parent chrysanthemum RELINDA is also made in this application. The new cultivar was discovered as a whole plant mutation in June 1996 by Rob Noodelijk in a controlled environment (greenhouse) in Rijsenhout Holland. The first act of asexual reproduction of 'RELINDA YELLOW' was accomplished when vegetative cuttings were taken from the initial selection in September 1996 in Rijsenhout Holland.

SUMMARY OF THE INVENTION

The present invention is a new and distinct variety of chrysanthemum bearing medium sized blooms with yellow ray-florets and yellow-green cushion.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
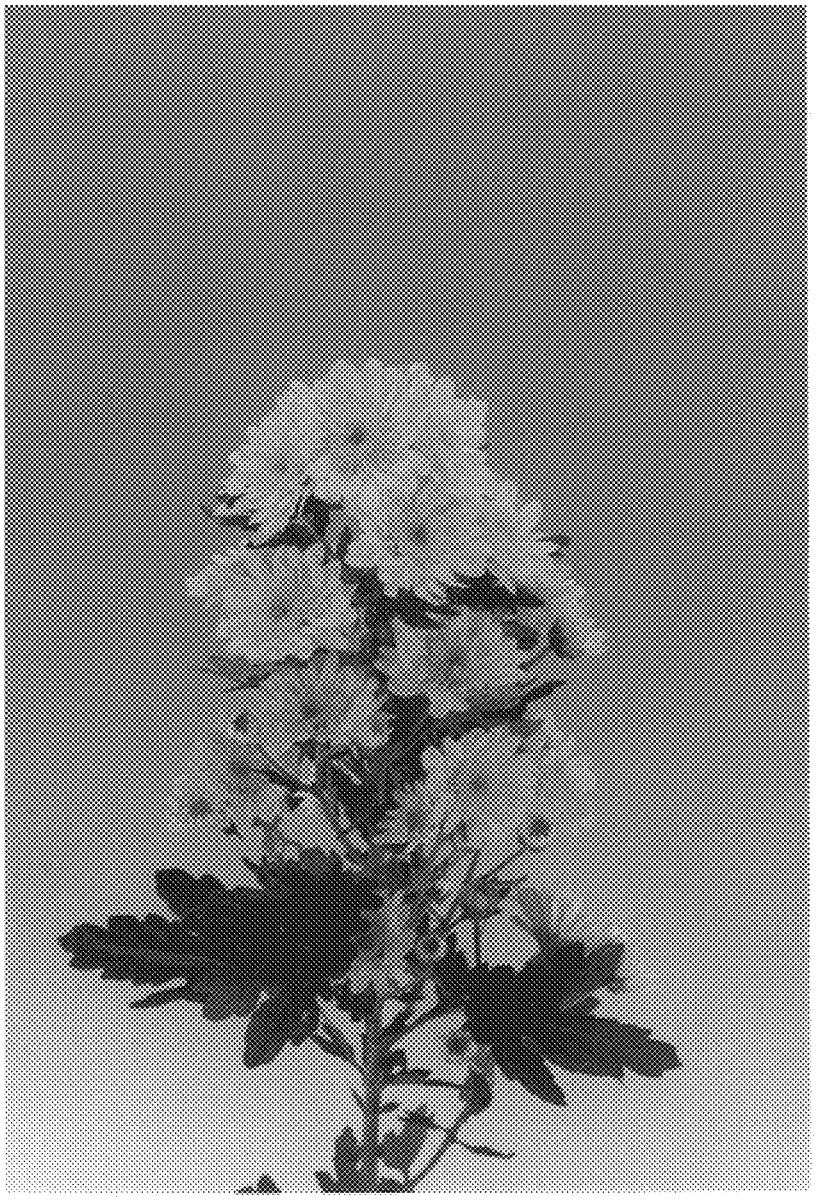
FIG. 1 shows a stem of the cultivar in full bloom.
Figure 2:
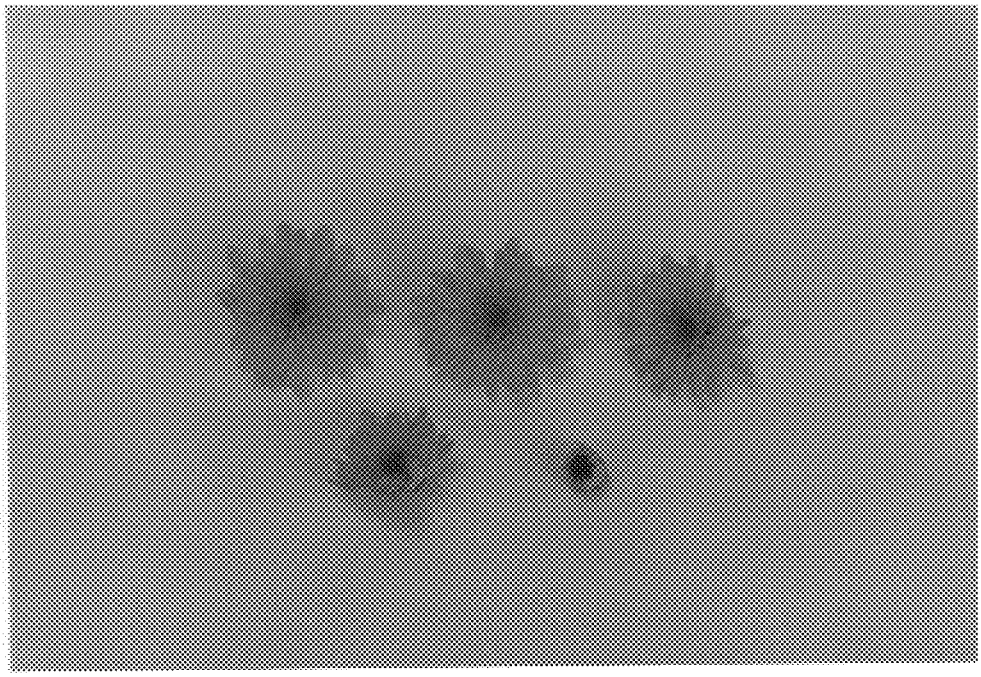
FIG. 2 shows the various stages of bloom of the new cultivar.
Figure 3:
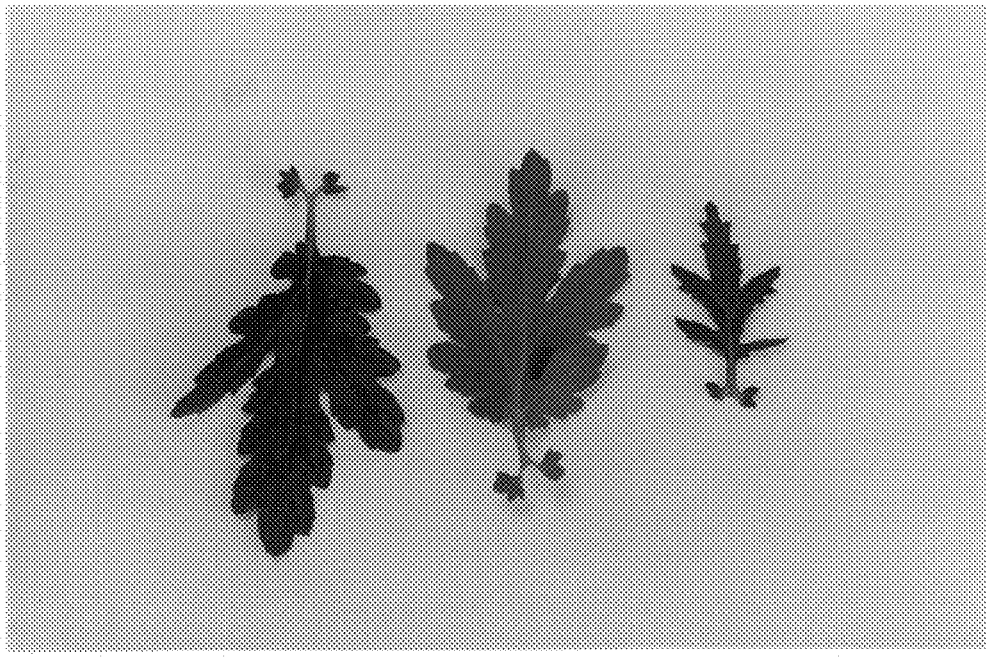
FIG. 3 shows the various stages of foliage and petiole of the new cultivar.

This new variety of chrysanthemum is of the botanical classification dendranthema grandiflora. The observations and measurements were gathered from 54 days plants grown in a greenhouse in Rijsenhout Holland in a photo-periodic controlled crop under conditions generally used in commercial practice. The greenhouse temperatures during this crop were at day-time between 18° C. and 25° C. and at night 20° C. After a long day period of 14 days the photo-periodic response time in this crop was 50 days. After the long day period to flowering growth retardants were applied 2 to 3 times in an average dose of 2.5 gram/liter water. The plants were observed (directly) during the flowering of this crop. No tests were done on disease or insect resistance or susceptibility. No tests were done on cold or drought tolerance. This new variety produces medium sized blooms with yellow ray-florets and yellow-green cushion blooming on the plant for 3 weeks. This new variety of chrysanthemum has been found to retain its distinctive characteristics throughout successive propagations however the phenotype may vary significantly with variations in environment such as light intensity and temperature. To show the phenotype as described 'RELINDA YELLOW' may be planted without assimilation lightning (high pressure sodium lamps) between week 50 and 40 of the next year under greenhouse conditions in Holland. With assimilation lightning (minimum level 2500 lux) it may be planted year round under greenhouse conditions in Holland.

From the cultivars known to inventor the most similar existing cultivar in comparison to 'RELINDA YELLOW' is RELINDA. When RELINDA and 'RELINDA YELLOW' are being compared the following differences and similarities are noticed: The difference of RELINDA and 'RELINDA YELLOW' is the yellow ray-floret color for which characteristic 'RELINDA YELLOW' has been selected out of 'RELINDA'. The ray-floret color of 'RELINDA' is white. All other characteristics of 'RELINDA YELLOW' and 'RELINDA' are similar.

The following is a description of the plant and characteristics that distinguish 'RELINDA YELLOW' as a new and distinct variety.

The color designations are taken from the plant itself. Accordingly, any discrepancies between the color designations and the colors depicted in the photographs are due to photographic tolerances. The color chart used in this description is: The Royal Horticultural Society color chart, edition 1995.

Botanical Description of CULTIVAR 'RELINDA YELLOW'

Bud:

*Size.*—Medium cross-section 1.2 cm height 1.4 cm.

*Outside color.*—Yellow 9 B.
*Involucral bracts.*—2 rows, length 7 mm, width 3 mm.
*Involucral bracts among disc-florets.*—Not present.
*Involucral bracts color.*—Yellow-green 146 B.

Bloom:
*Type.*—Anemone.
*Height.*—Flat.
*Size.*—Medium.
*Fully expanded.*—6.0–6.5 cm.
*Number of blooms per single stem.*—Average of 12.
*Performance on the plant.*—21 days.

Cultivar 'RELINDA YELLOW':
*Seeds.*—Not produced.
*Fragrance.*—Typical chrysanthemum.

Color:
*Center of the flower* (*disc-florets*).—Immature yellow-green 146 A mature yellow-green 146 A and yellow-orange 14 A at the edge.
*Color of upper surface of the ray-florets.*—Yellow 9 A.
*Color of the lower surface of the ray-florets.*—Yellow 9 B.
*Tonality from distance.*—A medium size clear yellow anemone with a clear green center.
*Discoloration to color.*—Yellow-orange 14 A.

Ray florets:
*Texture.*—Upper and under side smooth.
*Number.*—38–40 (2–3 rows).
*Cross-section.*—Convex.
*Longitudinal axis of majority.*—Straight, outer row reflexing.
*Length of corolla tube.*—Short.
*Ray-floret margin.*—Entire.
*Ray-floret length.*—3.0–3.3 cm.
*Ray-floret width.*—1.0 cm.
*Ratio length/width.*—Medium.
*Shape of tip.*—Rounded.

Disc florets:
*Disc diameter.*—1.2–1.5 cm.
*Distribution of disc florets.*—Numerous clearly visible at all stages of flowering.
*Shape.*—Petaloid.
*Color.*—Yellow-green 146 A.
*Receptacle shape.*—Domed raised.

Reproductive organs:
*Stamen* (*present in disc florets only*).—Yellow-green, thin, 4 mm in length.
*Number of stamen.*—Grown together as one.
*Stamen color.*—Yellow-green 144 B.
*Pollen.*—None.
*Styles* (*present in both ray and disc florets*).—Yellow-green, thin.
*Style color.*—Yellow-green 144 B.
*Style length.*—5 mm.
*Stigmas.*—Yellow-green 144 B.
*Stigma width.*—1 mm.
*Ovaries.*—Enclosed in calyx.

Plant:
*Type.*—Spray mum meant for erect culture. Herbaceous.
*Growth habit.*—Upright.
*Growth rate.*—Medium.
*Height.*—105–115 cm.
*Internodes.*—2.0–2.5 cm.
*Spray formation.*—Corymbiform.
*Stem color.*—Yellow-green 146 B.
*Stem strength.*—Strong.
*Stem brittleness.*—Absent.
*Stem anthocyanin coloration.*—Absent.
*Peduncle length.*—Near the top 10 cm, near the middle 14 cm, neat the bottom 20 cm.

Peduncle color:
*Flowering response* (*photo-periodic controlled crop, not natural season*).—50 days.

Foliage:
*Color.*—Upper side green 139 A under side green 137 A.
*Size.*—Medium to large; length 8.5 cm width 6.0 cm.
*Quantity* (*number per single stem*).—34–36.
*Shape.*—Ovate.
*Texture upper side.*—Fleshy and glabrous.
*Texture under side.*—Pubescent.
*Venation arrangement.*—Plamate.
*Shape of the margin.*—Serrated.
*Shape of base of sinus between lateral lobes.*—Round.
*Margin of sinus between lateral lobes.*—Converging.
*Shape of base.*—Attenuate.
*Apex.*—Mucronate.

Differences with the comparison Varieties

| | 'RELINDA YELLOW' | 'RELINDA' |
|---|---|---|
| Ray-floret color | Yellow 9 A | White 155 D |

I claim:

1. A new and distinct variety of chrysanthemum plant as described and illustrated.

* * * * *